United States Patent
Taira et al.

(10) Patent No.: US 10,806,585 B2
(45) Date of Patent: Oct. 20, 2020

(54) TRANSLUCENT IN-VIVO INDWELLING DEVICE AND UTILIZATION THEREOF

(71) Applicant: INTER-UNIVERSITY RESEARCH INSTITUTE CORPORATION NATIONAL INSTITUTES OF NATURAL SCIENCES, Mitaka-shi, Tokyo (JP)

(72) Inventors: Takunori Taira, Okazaki (JP); Yoichi Sato, Okazaki (JP); Junichi Nabekura, Okazaki (JP); Hiroaki Wake, Okazaki (JP)

(73) Assignee: INTER-UNIVERSITY RESEARCH INSTITUTE CORPORATION NATIONAL INSTITUTES OF NATURAL SCIENCES, Tokyo (JP)

( * ) Notice: Subject to any disclaimer, the term of this patent is extended or adjusted under 35 U.S.C. 154(b) by 0 days.

(21) Appl. No.: 15/529,939

(22) PCT Filed: Nov. 27, 2015

(86) PCT No.: PCT/JP2015/083492
§ 371 (c)(1),
(2) Date: May 25, 2017

(87) PCT Pub. No.: WO2016/084961
PCT Pub. Date: Jun. 2, 2016

(65) Prior Publication Data
US 2017/0325961 A1 Nov. 16, 2017

(30) Foreign Application Priority Data
Nov. 28, 2014 (JP) ................................ 2014-242148

(51) Int. Cl.
*A61F 2/28* (2006.01)
*A61L 27/50* (2006.01)
(Continued)

(52) U.S. Cl.
CPC ................ *A61F 2/28* (2013.01); *A61L 27/00* (2013.01); *A61L 27/12* (2013.01); *A61L 27/50* (2013.01);
(Continued)

(58) Field of Classification Search
CPC .......... A61F 2/28; A61F 2/2875; A61L 27/00; A61L 27/12; A61L 27/50; A61N 5/0622
See application file for complete search history.

(56) References Cited

U.S. PATENT DOCUMENTS 5,418,640 A * 5/1995 Hood .................... G02F 1/0102
359/240
5,952,253 A * 9/1999 Dejneka .................. C03C 10/16
501/10
(Continued)

FOREIGN PATENT DOCUMENTS

JP H09-249515 A 9/1997
JP 2002-512584 A 4/2002
(Continued)

OTHER PUBLICATIONS

Investigation on the structure and upconversion fluorescence of Yb31/Ho31 co-doped fluorapatite crystals for potential biomedical applications, Li et al., Scientific Reports, 4:4446, DOI: 10.1038/srep04446.*
(Continued)

*Primary Examiner* — John R Downey
(74) *Attorney, Agent, or Firm* — Oliff PLC

(57) ABSTRACT

A translucent in-vivo indwelling device with a translucent region including a rare earth doped fluorapatite.

14 Claims, 7 Drawing Sheets

(51) Int. Cl.
  *A61L 27/12* (2006.01)
  *A61L 27/00* (2006.01)
  *A61N 5/06* (2006.01)
  *C03C 10/16* (2006.01)
  *B28B 1/00* (2006.01)

(52) U.S. Cl.
  CPC ............ *C03C 10/16* (2013.01); *A61F 2/2875* (2013.01); *A61L 2430/02* (2013.01); *A61L 2430/32* (2013.01); *A61N 5/0622* (2013.01); *B28B 1/00* (2013.01)

(56) References Cited

U.S. PATENT DOCUMENTS

| | | | | |
|---|---|---|---|---|
| 6,130,178 | A * | 10/2000 | Andrus | C03C 10/16 501/3 |
| 6,539,944 | B1 * | 4/2003 | Watson | A61B 18/20 128/898 |
| 2002/0151903 | A1 * | 10/2002 | Takei | A61F 2/0805 606/99 |
| 2008/0144671 | A1 * | 6/2008 | Ershov | G03F 7/70583 372/5 |
| 2010/0069455 | A1 * | 3/2010 | Takato | A61F 2/2875 514/406 |
| 2011/0260367 | A1 | 10/2011 | Taira et al. | |
| 2013/0165846 | A1 * | 6/2013 | Peyman | A61N 5/062 604/20 |
| 2013/0292882 | A1 | 11/2013 | Taira et al. | |
| 2013/0309278 | A1 * | 11/2013 | Peyman | A61K 41/00 424/400 |
| 2013/0320277 | A1 | 12/2013 | Taira et al. | |
| 2014/0330123 | A1 * | 11/2014 | Manwaring | A61B 8/0808 600/438 |

FOREIGN PATENT DOCUMENTS

| | | |
|---|---|---|
| JP | 2012-024113 A | 2/2012 |
| JP | 2012-166433 A | 9/2012 |
| WO | 2010/073712 A1 | 7/2010 |

OTHER PUBLICATIONS

Transparent Alumina: A Light-Scattering Model?, R. Apetz and M. P. B. van Bruggen, J. Ameri. Ceram. Soc. voi. 86, No. 3,480-486 (2003) (Year: 2003).*

Ceramics 43, pp. 984-986, No. 11, (2008).

Inada, Hiroyuki et al., "Chusu Shinkei Kei no 2 Koshi Reiki in vivo imaging.", Experimental Medicine separate volume, in vivo Imaging Jikken Protocol, pp. 171-180, (2013).

Hasegawa, Ryohei P., "Development and Future of Brain-Machine Interface.", Journal of the Institute of Electronics, Information and Communications Engineers, pp. 1066-1075, vol. 91, No. 12, (2008).

Cho, Oshi et al., "A Novel Europium Doped Apatite/Wollastonite Porous Magnetic Bioactive Glass Ceramic.", Seibutsu Igaku Kotei Gakkaishi, pp. 785-789, vol. 24, (2007).

Payne, Stephen A. et al., "Laser, Optical, and Thermomechanical Properties of Yb-doped Fluorapatite.", IEEE Journa of Quantum Electronics, pp. 170-179, vol. 30, No. 1, (1994).

Akiyama, Jun et al., "Laser Demonstration of Diode-Pumped Nd3+-Doped Fluorapatite Anisotropic Ceramics.", Applied Physics Express, pp. 022703-1 to 022703-3, vol. 4, (2011).

Jan. 12, 2016 International Search Report issued in Patent Application No. PCT/JP2015/083492.

May 30, 2017 English Translation of the IPRP issued in Patent Application No. PCT/JP2015/083492.

Jul. 31, 2018 Office Action issued in Japanese Application No. 2014-242148.

* cited by examiner

TRANSLUCENT IN-VIVO INDWELLING DEVICE AND UTILIZATION THEREOF

TECHNICAL FIELD

The specification is related to translucent in-vivo indwelling device and use therefor.

This application is related to Japanese Patent Application No. 2014-242148 filed on Nov. 28, 2014 and claims priority to the Japanese application entire contents of which are incorporated by reference herein.

BACKGROUND ART

Conventionally, parts of the human body have been replaced with artifacts such as artificial bones and artificial joints to improve or maintain biological functions associated with the replacement site. Moreover, treatment of central nervous system diseases is now being carried out by applying external electrical stimulation using electrodes or the like placed on the brain. Hydroxyapatite is a component of vertebrate bone that is conventionally used in artificial bone and the like. Hydroxyapatite (HAp) is a basic calcium phosphate represented by the chemical formula $Ca_{10}(Po_4)_6(OH)_2$, and is a principal component of natural bones and teeth (Non Patent Literature 1).

Moreover, for example the inside of the brain is now being observed and controlled by excising the skull and installing a transparent window to permit microscopic observation with introduced laser light. That is, by focusing an ultra short pulse laser on a specific part of the brain via a glass window, it is possible to observe the luminescence produced by the multiphoton absorption process of fluorescent proteins, or control the activity of nerve cells to a high degree using photoactive substances. Glass is currently used as a window material (Non Patent Literature 2).

In recent years, a technology called brain-machine interface (BMI) has come under increased scrutiny. BMI is a technology Whereby brain function is assisted or regulated by a machine, or the brain is artificially connected to a machine (Non Patent Literature 3).

CITATION LIST

Non Patent Literature 1: Ceramics 43 (2008), No. 11, 984-986
Non Patent Literature 2: "Two-photon excitation in-vivo imaging of the central nervous system", Experimental Medicine Supplement, Experimental Protocols for In-vivo Imaging, Yodosha, November 2012, 171-180
Non Patent Literature 3: Journal of the Institute of Electronics, Information and Communications Engineers, Vol. 91, No. 12, 2008, 1066-1075

SUMMARY OF INVENTION

An artificial device to be indwelled in a living body is required to be biocompatible so as not to be rejected by the immune systems of the host in which it is placed. It also needs to have chemical stability and strength so that it can stably maintain its shape and function even in vivo.

In the case of treatment, research and BMI using laser light or photostimulation, a device must have stable translucency sufficient to transmit light.

Although hydroxyapatite has excellent biocompatibility, however, it is not translucent. Glass on the other hand has poor biocompatibility and tends to provoke an immune response, resulting in a dramatic decrease in initial translucency.

It is therefore an object of this Description to provide a translucent in-vivo indwelling device, and a use therefor.

Solutions To Technical Problem

The inventors discovered that a material of rare earth doped fluorapatite having at least a certain density can be used to construct a translucent in-vivo indwelling device that exhibits a low level of light scattering loss and is not only biocompatible but also has excellent strength and chemical stability. Moreover, because a rare earth doped fluorapatite can maintain its translucency with respect to the living body, it can allow not only the output of information from inside to outside the living body, but also the input of information from outside to inside the living body. The present Description provides the following means based on these findings.

(1) An in-vivo indwelling device comprising a translucent region containing a rare earth doped fluorapatite.

(2) The in-vivo indwelling device according (1), wherein the rare earth doped fluorapatite has a linear transmittance of at least 50%.

(3) The in-vivo indwelling device according to (1) or (2), wherein the rare earth doped fluorapatite has a porosity of less than 0.2%.

(4) The in-vivo indwelling device according to any of (1) to (3), wherein the rare earth doped fluorapatite undergoes laser oscillation.

(5) The in-vivo indwelling device according to any of (1) to (4), which is a bone replacement device.

(6) The in-vivo indwelling device according to any of (1) to (4), which is an optical device for the brain.

(7) The in-vivo indwelling device according to (6), which is an optical window.

(8) The in-vivo indwelling device according to (6), which is for monitoring purposes.

(9) The in-vivo indwelling device according to (6), which is for purposes of light illumination from the outside.

(10) A system for inputting and outputting information to and from a living body, the system comprising: a base material having a translucent region containing a rare earth doped fluorapatite; and a device for outputting information from inside the living body through this base material via the medium of light or for inputting information from outside the living body through this base material via the medium of light.

(11) The system according to (10), which targets the brain.

(12) The system according to (10) or (11), wherein the light is laser list.

(13) The system according to any of (10) to (12), which is an input and output system for therapeutic purposes.

(14) A method for inputting and outputting information to and from a living body, the method comprising a step of either outputting information from inside the living body via the medium of light through an in-vivo indwelling base material having a translucent region containing a rare earth doped fluorapatite, or inputting information from outside the living body via the medium of light through this base material.

(15) A method for operating a system according to any of (10) to (13), wherein the system comprises a step of either outputting information from inside the living body via the medium of light through an in-vivo indwelling base material having a translucent region containing a rare earth doped fluorapatite, or inputting information from outside the living body via the medium of light through this base material.

BRIEF DESCRIPTION OF DRAWINGS

FIG. 7 gives examples of uses of the device and the like;

DESCRIPTION OF EMBODIMENTS

Figure 1:
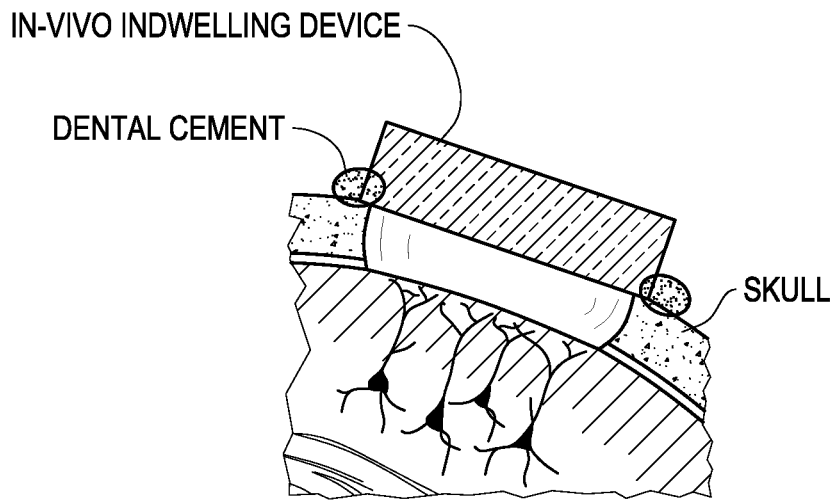
FIG. 1 shows one example of the device indwelling in a living body.

The present Description relates to a translucent in-vivo indwelling device (hereunder also called simply "the device"), and to a use therefor. A translucent in-viva indwelling device with excellent biocompatibility and the like can be provided with the device. Due to these properties, the device is suited to long-term indwelling because it is minimally invasive and maintains its translucency in vivo.

By indwelling the device in a living body, it is possible to replace bone and the like because of the biocompatibility, chemical stability, strength and the like of the device.

Moreover, when the device is indwelled in a living body it can stably maintain its translucency in vivo because of its good biocompatibility, translucency, chemical stability, strength and the like. In vivo monitoring and imaging can therefore be accomplished via the device in a state closer to the original physiological state. That is, it makes it possible to obtain and read out (output) information from inside a living body.

When the device is indwelled in a living body, moreover, information from outside the living body can be read in (input) to the living body based on light supplied from the outside via the device.

Moreover, when the device is indwelled in a living body it is possible to exploit the properties of rare earth elements as photoactive elements by subjecting the device to laser oscillation and inputting information into the living body based on laser light.

In particular, because the device has excellent adhesiveness to bone in addition to chemical stability and strength in vivo, it can be substituted for part of a bone as discussed above and used as an interface for information from inside and outside the living body.

Although hydroxyapatite has conventionally been known for good biocompatibility with bone and teeth, the biocompatibility and adhesiveness of fluorapatite with bone and teeth has not necessarily been well established. Moreover, the fluorapatite used in the device is not porous like conventional hydroxyapatite, but instead its crystallinity is controlled to make it both dense and translucent. Conventionally, the biocompatibility and affinity of hydroxyapatite have been attributed to its porosity, which causes it to be infiltrated by cells and intercellular substances.

Not only does the fluorapatite of this disclosure not have such a porous structure to provide good biocompatibility and bone adhesiveness, but the biocompatibility of the material itself it unclear, and in fact there have been no reports at all on the biocompatibility of rare earth doped fluorapatites. Consequently, the biocompatibility and bone adhesiveness of the rare earth doped fluorapatite used in the device cannot be inferred from prior art, and were even difficult for those in the art to predict.

The device uses a translucent region having a matrix of fluorapatite. This device can be used as an in vivo indwelling device in vertebrates including mammals. The type of vertebrate is not particularly limited, but is preferably a mammal such as a human. Examples of mammals other than humans include experimental animals such as pigs, dogs, cats, rabbits, mice, monkeys and the like.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and inventions to provide a further improved translucent in-vivo indwelling device and use therefor or the like.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

Figure 2:
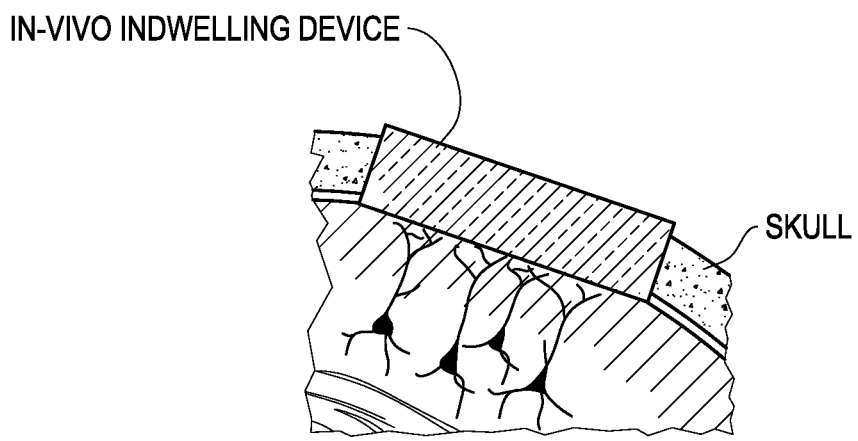
FIG. 2 shows another example of the device indwelling in a living body.

The device and uses therefor are explained in detail below with reference to the appropriate drawings. FIG. 1 shows one example of the device indwelling in a living body, FIG. 2 shows another example of the device indwelling in a living body, and FIGS. 3 to 6 show application examples of the device. The rare earth doped fluorapatite used in the device is explained first, after which the device itself and its in vivo applications are explained.

(In Vivo Indwelling Device)

(Rare Earth Doped Fluorapatite)

Translucent rare earth doped fluorapatites in themselves are well known. A rare earth doped fluorapatite with translucent properties can be used in the present disclosures. The rare earth doped fluorapatite may be a polycrystalline material or a single crystal material. In the case of a polycrystalline material, the crystal axes are oriented uniaxially or controlled to a certain extent to provide translucency and permit laser oscillation. In uniaxial crystals of apatite and the like, the c-axis direction is given as the principal crystal axis direction. WO 2010/073712 and Japanese Patent Application Laid-open. No. 2012-466433 disclose rare earth doped fluorapatites (polycrystalline materials) whose crystal axes are oriented. It is known both from these patent references and from various other documents that such rare earth doped fluorapatites can undergo laser oscillation (Applied Physics Express 4 (2011) 022703, IEEE Journal of Quantum Electronics Vol. 30, No. 1, January 1994, 170-179).

Fluorapatite has the general formula $\alpha_5(\beta O_4)_3\gamma$ (in which α represents Ca or Sr, β represents P or V, and γ represents F). Specifically, it is represented as $Ca_5(PO_4)_3F$, $Sr_5(PO_4)_3F$, $Ca_5(VO_4)_3F$ or $Sr_5(VO_4)_3F$.

The rare earth element to be doped is not particularly limited. Examples of rare earth elements used in doping include cerium (Ce), praseodymium (Pr), neodymium (Nd), promethium (Pm), samarium (Sm), terbium (Tb), dysprosium (Dy), holmium (Ho), erbium (Er), thulium (Tm) and ytterbium (Yb). One of these rare earth elements may be contained in the single crystal particles of the fluorapatite, or multiple kinds of rare earth elements may be included in the single crystal particles. Of these rare earth elements, the single crystal particles preferably contain at least one of Nd and Yb, which are typical elements used in doping solid lasers in particular.

A fluorapatite doped with a rare earth element can be manufactured by a know method of preparing a suspension containing one or two or more single crystal particles having a rare earth doped fluorapatite, in which a rare earth element is uniformly dispersed, and casting this suspension in a magnetic field space and molding the same with the crystal particles aligned, and then firing the same. The rare earth doped apatite used in the device can be obtained with reference to WO 2010/073712, Japanese Patent Application Laid-open No. 2012466433 or the like, as necessary. A rare earth doped fluorapatite of a size and shape suited to the device can be easily obtained by this manufacturing method.

The rare earth doped fluorapatite preferably has a specific translucency. The standard for translucency may be linear transmittance and/or porosity. The rare earth doped fluorapatite used in the device preferably has a linear transmittance of at least 50%. In vivo monitoring and laser oscillation are possible if the linear transmittance is at least 50%. The linear transmittance is more preferably at least 60%, or still more preferably at least 70%, or yet more preferably at least 80%. The linear transmittance $T_1$ of the rare earth doped fluorapatite is evaluated by irradiating a specimen perpendicularly with light of power $I_0$ directed straight and in parallel, then calculating $T_1 = I_1/I_0 \times 100(\%)$ with $I_1$ being the power of the light that passes straight through the sample in parallel to the original optical path without spreading. The linear transmittance $T_1$ can be measured using a commercial UV-visible spectrophotometer (such as JASCO Corporation V-700, V-7000 or the like). When measuring the linear transmittance, the incident surface and emission surface of the measurement light in the sample are preferably parallel and optically polished in order to exclude the effects of diffuse reflection and refraction of the light and the like on the specimen surface.

The rare earth doped fluorapatite preferably has a porosity of less than 0.2%. In vivo monitoring and laser oscillation are possible if the porosity is less than 0.2%. The porosity is more preferably 0.1% or less, or still more preferably 0.05% or less. The porosity of the rare earth doped fluorapatite is the (total) porosity including closed pores. Consequently, porosity can be determined as (true density−sintered body density)/true density. The sintered body density here is a number obtained by dividing the weight of the sample by the external volume as defined in JIS R 1634:1998. The true density is the density of an ideal crystal, and can be calculated from the molecular weight and crystalline structure.

The rare earth doped fluorapatite preferably has a light scattering loss factor of 0.1 $mm^{-1}$ less. With such a light scattering loss factor, the material is even more suitable for in vivo monitoring and laser oscillation. The light scattering loss factor of the rare earth doped fluorapatite can be calculated based on the following formula from the linear transmittance $T_1$ and the refractive index n of the sample to light:

$$\text{Light scattering loss factor } \sigma = -\ln(1-T_1-(((n-1)^2+1)/((n+1))^2)/L$$

(wherein L is the thickness (cm) of the specimen).

Such a translucent rare earth doped fluorapatite may be used as a laser medium based on the rare earth element (see WO 2010/07371, Japanese Patent Application Laid-open No. 2012-166433 or the like).

(Device Type and In-Vivo Indwelling)

The device may be provided with a translucent region containing a rare earth doped fluorapatite. The translucent rare earth doped fluorapatite used in the device as described above is contained in at least a partial region, and has translucency in that region. The configuration of the device is not particularly limited, and various forms may be adopted according to the application site in the living body and the use of the device. Only some region or regions of the device may be composed of the rare earth doped fluorapatite, or all regions of the device may be composed of the rare earth doped fluorapatite.

The device itself may be indwelled in vivo because it has excellent biocompatibility and the like, and it can be attached to bone and indwelled in vivo because it has excellent bone adhesiveness. Although the device itself has bone adhesiveness, a known dental cement or adhesive for living tissue may be used as necessary in the area of contact with bone or the like early adhesion with the bone or the like. The c-axis direction of the rare earth doped fluorapatite crystal in the device may or may not follow the c-axis direction of the apatite crystals in the bone during in-vivo indwelling. This is because the c-axis direction of the apatite crystals in the bone at the indwelling site is not necessarily uniaxial, the surrounding environment is not necessarily uniform, and different adhesive materials and the like may be used. Consequently, the c-axis direction and the like of the biological apatite at the indwelling site may be considered in selecting the c-axis orientation of the rare earth doped fluorapatite in the indwelling device and applying it to the indwelling site.

(Bone Replacement Device)

The device may be used as a bone replacement device. A bone replacement device replaces bone parts in humans and other animals, restoring and improving their function. When the device is intended for use with bone, it may be configured with only a rare earth doped fluorapatite constituting all regions to be substituted for all or part of a specific bone part. Alternatively, the rare earth doped fluorapatite may be used only for the regions designed for light transmission and laser oscillation, and another conventional material (for example, metal or another ceramic such as hydroxyapatite) may be used for the other regions.

The bone replacement device is not particularly limited, and may take a form that can be substituted for all or part of various bone parts in humans and other animals. For example, the device may be used as a bone replacement device such as those conventionally used in plastic surgery, neurosurgery and oral surgery. Typically, it may be used as all or part of a human or other cranial plate, all or part of a burr-hole button, all or part of an ilium, all or part of a cervical spine or block, all or part of a lamina, all or part of a spinous process, all or part of a pituitary plate, all or part of a mandible or maxilla, or all or part of an alveolar bone or the like.

In particular, when used as a bone replacement device to replace all or part of a cranial plate or burr-hole button, the device is useful as an optical device or interface to allow monitoring inside the brain and the like.

For example, as shown in FIG. 1, the device can be used as a bone replacement device that is indwelled as a replacement for part of a skull or the like. Alternatively, as shown in FIG. 2, it can be used as a bone replacement device that is indwelled so as to cover a bone defect. The embodiments shown in. FIGS. 1 and 2 are mainly useful in the case of skull located near the body surface.

(Optical Device)

The device can be used as an optical device (optical window) for outputting information from inside to outside a living body and inputting information from outside to inside a living body via the medium of light. The mode of indwelling of the device in vivo is not particularly limited, and may be any mode that allows it to function as an optical device. In the case of skull applications for example, modes such as those shown in FIGS. 1 and 2 may be used.

The concept of light here is not particularly limited, and may be interpreted in the broadest sense. Typical examples include visible light, ultraviolet light, infrared light, X-rays, laser light and the like.

Information from inside a living body via the medium of light may be any information that can be obtained from inside a living body via the medium of light, without any particular limitations, and examples include observations of cells, tissues, organs, body parts, and the dynamics of blood and other bodily fluids and drugs and the like. When obtaining information from inside a living body, a stimulus (electrical stimulus, sensory stimulus, motor stimulus or the like) is sometimes applied in advance from outside the body. Such an external stimulus may be supplied through the device via the medium of light when the device is an optical device. Information about cells and the like and drug dynamics and the like is easier to obtain if they are made visible by, for instance, labeling them with a specific substance or the like, either by administering a drug or by genetic engineering techniques. Examples of such methods are disclosed in "Two-photon excitation in-vivo imaging of the central nervous system" (Experimental Medicine Supplement, Experimental Protocols for In-vivo Imaging, Yodosha, November 2012, 171-180) and the like.

Figure 3:
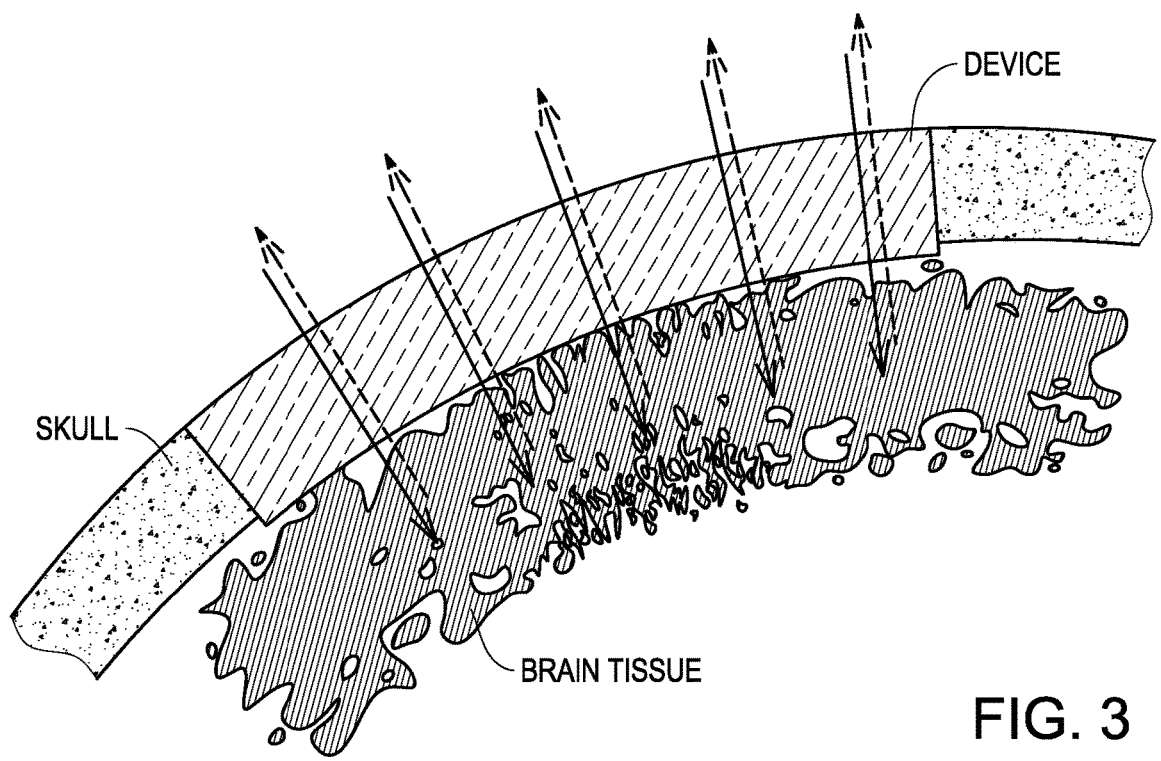
FIG. 3 shows an example of the device undergoing laser oscillation.

FIG. 3 shows an application example of the device as an optical device. As shown in Eta 3, the device is indwelled in the skull, either near or in contact with the brain tissue. Because the device is translucent, it can function as an optical window or the like to allow laser light or the like from outside to reach the in vivo tissue. The device can also receive signal light from tissue or a substance present in tissue in response to such incident light from the outside.

Figure 4:
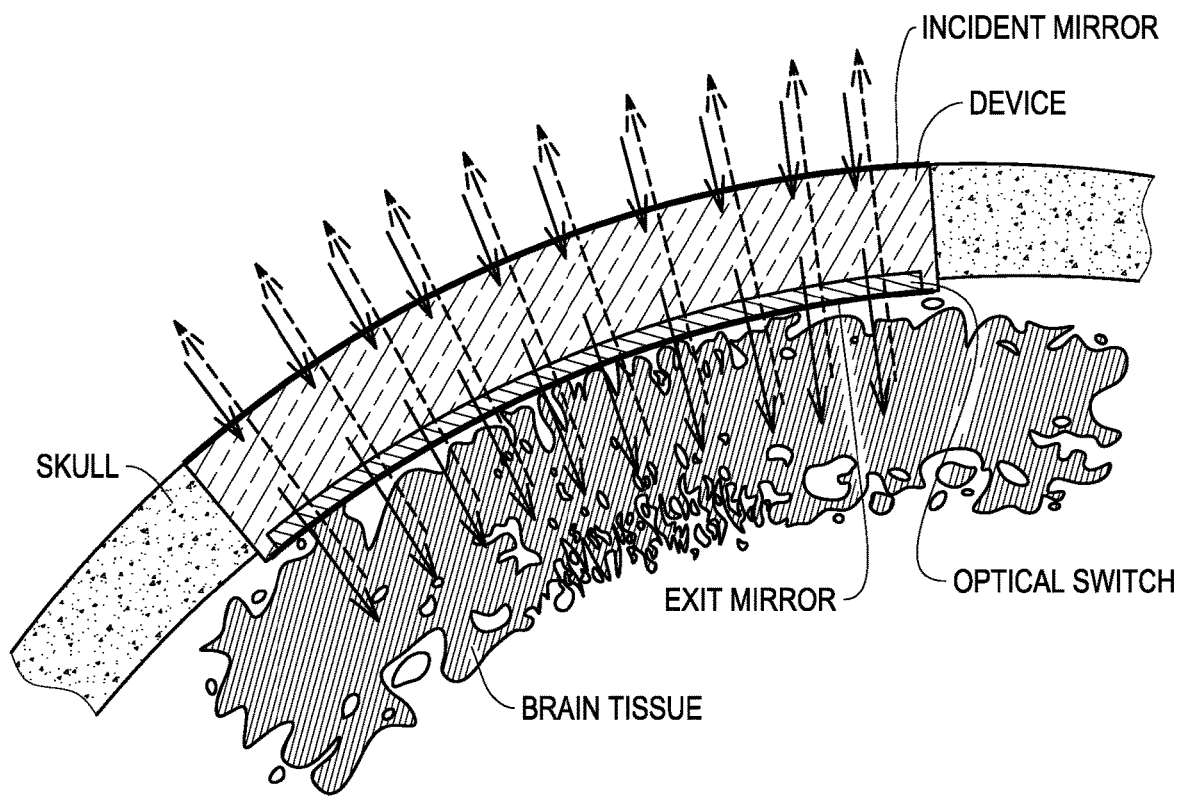
FIG. 4 shows an example of the device undergoing laser oscillation.
Figure 5:
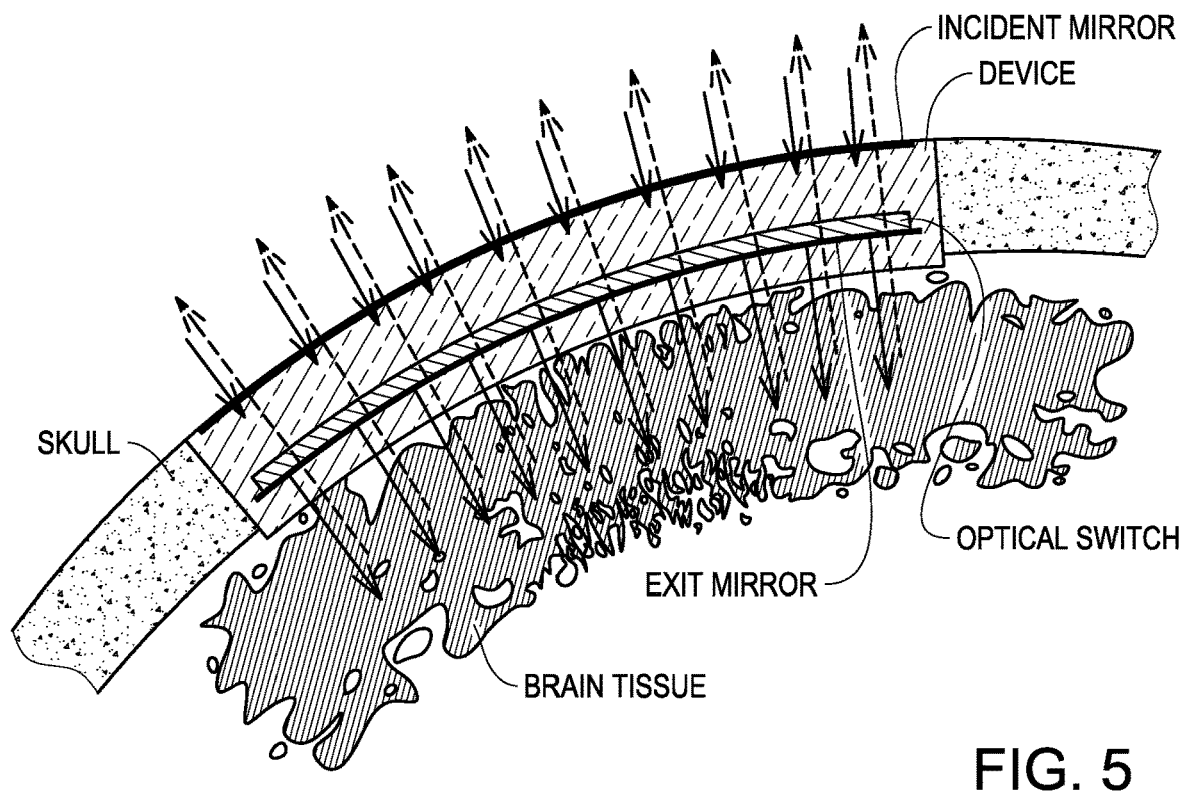
FIG. 5 shows an example of the device undergoing laser oscillation.
Figure 6:
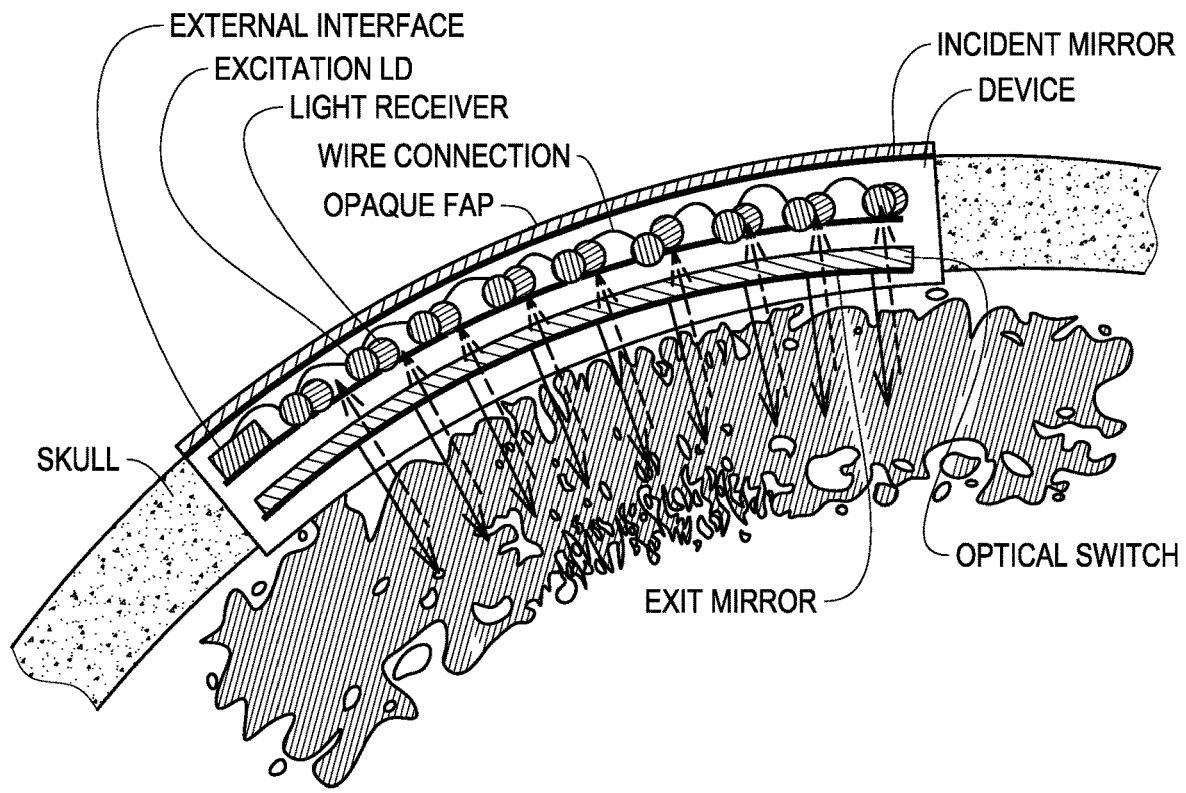
FIG. 6 shows an example of the device undergoing laser oscillation.

In the embodiment shown in FIG. 3, microchip lasers (oscillators) and/or light receivers can be provided near or in contact with the outer surface of the device to thereby construct a wearable in-vivo indwelling laser oscillation device comprising the device as an optical window. In this case, the microchip lasers can be disposed in an array relative to the outer surface of the device to thereby construct a 2D array in-vivo indwelling laser oscillation device. As discussed below, the embodiments of FIGS. 4 to 6 are also optical devices.

(Monitoring Applications)

A typical example of a use of the device for outputting information from inside the living body is a monitoring application for monitoring information inside the living body. When used for a monitoring application, the device is indwelled in vivo so as to allow monitoring of the inside of the body. Typically, as in the case of the aforementioned optical device, it becomes an intracerebral monitoring device when used as all or part of a cranial plate or all or part of a burr-hole button.

Information from inside the living body can be obtained either with the naked eye or with various kinds of detection equipment and microscopes. This information can also be Obtained via the device with a confocal laser scanning microscope for biology or a multi-lattice excitation laser scanning microscope, which observe the inside of the living body by irradiating it with a laser from the outside. The modes of application given as examples in FIGS. 1 to 3 above and FIGS. 4 to 6 below may also be used for monitoring purposes.

Information from outside the living body via the medium of light may be any information that can be supplied from outside the living body via the medium of light, without any particular limitations, and examples include various kinds of light stimulus. Such information, from outside the living body may also be various kinds of light such as infrared light and laser light capable of stimulating neurons and other cells, tissues, organs and the like. It may also be various kinds of light (stimulus) capable of activating or inactivating substances inherent in the living body. A light stimulus may also be for purposes of activating, inactivating or detecting a substance that has been made in advance to exist in the living body, either by genetic engineering techniques or by administration or the like. Based on photoelectric, activated ion channels such as channelrhodopsin 2 and halorhodopsin are known for activating biological substances with light (Deisseroth K, Feng G, Majewska A K, Miesenbock G, Ting A, Schnitzer M J. *Next-generation optical technologies for illuminating genetically targeted brain circuits. J Neurosci.* 2006 Oct. 11; 26(41):10380-6, Wu Y I, Frey D, Lunqu O I, Jaehriq A, Schichting I, Kuhlman B, Hahn K M. *A genetically encoded @photoactivatable RAc controls the motility of living cells. Nature* 2009 Sep. 3; 461(7260):104-8.).

(Therapeutic Applications, Research Applications and the Like Using Light Illumination from the Outside)

Examples of applications of the device for inputting information from outside to inside the living body include optical windows for applying light stimulus as information from outside to inside the living body. The device can thus be used for, for instance, therapeutic (including care based on functional improvement and welfare applications) and research uses. Examples of therapeutic applications include those in which infrared or laser light is transmitted to the living body from the outside via the device to activate cells or tissues. For example, it has been reported that the causal proteins of Alzheimer's disease and Parkinson's disease have been inactivated by specific laser light.

Therapeutic effects against Parkinson's disease have also been reported using a Femto laser, by intracerebrally administering a liposome containing dopamine and having an attached metal nanoparticle, and then exposing this to a Femto laser to cause the dopamine to be released from the liposome.

Based on photogenetics, moreover, in addition to channelrhodopsin and halorhodopsin (see above), which are proteins that are photoactivated by light stimulation, nerve cells and other cells can be controlled for example by using light-gated ionotropic glutamate receptors (Molecular Therapy, Vol. 19, No. 9, July 2011, 1212-1219), light-dependent ionotropic glutamate receptors (Molecular Therapy, vol. 19, no. 9, July 2011, 1190-1192), 1212-1219 and the like (for the general theory, see Biol. Psychiatry 012, 71, 1020-1032).

Such therapeutic applications are applicable as is to the development of therapeutic methods and to research for analyzing functions.

All of the various applications of the device described above are especially useful as brain applications when the device is indwelling in the skull. For example, the modes of use shown in FIGS. 1 to 3 and FIGS. 4 to 6 can be used by preference.

For these reasons, the device is useful as an input-output interface for information transmitted via the medium of light (information from outside the living body and information from inside the living body).

(Laser Oscillation Device)

Because rare earth doped fluorapatite is a laser medium, the device can be used as a part of a laser oscillation device (laser medium).

When the device is used as a laser oscillation device—a kind of optical device, the embodiments thereof are not particularly limited, and for example the embodiments shown in FIG. 4 and FIG. 5 may be adopted. In the embodiments shown in FIG. 4 and FIG. 5, the device is indwelled as a replacement for part of the skull, an incident mirror is disposed on the body surface side of the device, and an exit mirror is provided on the internal surface side of the device. An optical switch is also provided on the outer side of the incident mirror. The incident mirror, exit mirror and optical switch may be provided on the outside of the device as shown in FIG. 4, or they may be provided in advance within the ceramic matrix of the device as shown in FIG. 5. The exit mirror may be omitted by substituting a Fresnel reflection. The optical switch may also be omitted. When a specific excitation light is supplied from the outside to a laser oscillation device of this kind, the device can function as a laser medium, oscillating the laser light and supplying a biological tissue (brain tissue) with laser light from the outside. Alternatively, as in FIG. 3, a signal light can be obtained from the in vivo tissue in response to the oscillated laser light. A reflection mirror and an output mirror are installed. Laser oscillation can be ensured by supplying the necessary light from the outside to the device.

In these embodiments, excitation light oscillation devices such as LDs may be provided on the outermost body surface side of the device. The excitation light oscillation devices can also oscillate the laser in the form of a 2D array when the oscillation part is configured as an array.

The embodiment shown in FIG. 6 may also be adopted for example when the device is used as a laser oscillation device. The embodiment shown in FIG. 6 is provided with an incident mirror on the body surface side within the device, and an exit mirror on the internal surface side, also within the device. An optical switch is also provided on the outside of the exit mirror within the device. In this embodiment, moreover, excitation LDs as excitation light oscillation devices may be disposed within the device on the outer side of the incident mirror. This allows laser oscillation to occur within the device as a bone replacement. As shown in FIG. 6, the excitation LDs may be provided as a linear or matrix array, and light receivers may also be provided at the same time. This enables a wide range of laser oscillation and light reception in any location. The excitation LDs and light receivers may be connected as necessary to the outside via an interference for purposes of supplying electricity and controlling input and output. The exit mirror and optical switch may also be omitted in this embodiment. Moreover, efficient laser oscillation can be achieved in this embodiment by covering the device with an opaque ceramic, such as a highly biocompatible opaque fluorapatite (FAP) or apatite.

Novel treatment methods can be anticipated when this device is used as a laser oscillation device because it allows direct laser oscillation of the inside of the living body from within the body rather than by laser irradiation from a laser oscillation device located outside the living body. That is, the therapeutic applications and the like mentioned above that use the device as an optical window for light irradiation can be achieved by means of laser oscillation from the device itself.

(System for Inputting and Outputting Information To and From a Living Body)

The system of these disclosures for inputting and outputting information to and from a living body may comprise a base material having a translucent region containing a rare earth doped fluorapatite, together with a device for outputting information from inside the living body through this base material via the medium of light or for inputting information from outside the living body through this base material via the medium of light. With this system, information can be input and output via the medium of light using a base material having a translucent region containing a rare earth doped fluorapatite (the device) as an optical window. Because the rare earth doped fluorapatite is not only biocompatible but also has excellent strength and chemical stability, it can stably maintain its translucency, and function as a good optical window for easy input and output of in vivo information.

The device described above can be used in the various embodiments explained above as the base material of this system. Moreover, in this system the device can be applied to the animals, locations, applications and the like explained above.

The input-output device of this system may be any input-output device that uses light as a medium. As described above, typical examples include various light irradiation devices, microscopes and detection devices that are applicable to the device.

Consequently, this system is preferably used as an input-output system targeting the brain. Moreover, this system is preferably an input-output system for purposes of therapy or care. Various kinds of light including laser light may be used as the light.

(Method for Inputting and Outputting Information To and From a Living Body)

The method of these disclosures for inputting and outputting information to and from a living body may comprise a step of either outputting information from inside the living body via the medium of light through an in-vivo indwelling base material (the device) having a translucent region containing a rare earth doped fluorapatite, or inputting information from outside the living body via the medium of light through this base material. Like the system, this method allows in vivo information to be easily input and output via the medium of light using the device as a good optical window.

Thus, because the device functions as a laser medium in addition to having good biocompatibility and translucency, it can provide not only an excellent optical window or the like, but also an interface for inputting and outputting light or for inputting and outputting information from inside and outside the living body via the medium of light. The device is also useful because it has excellent biocompatibility and is thus minimally invasive.

Figure 7:
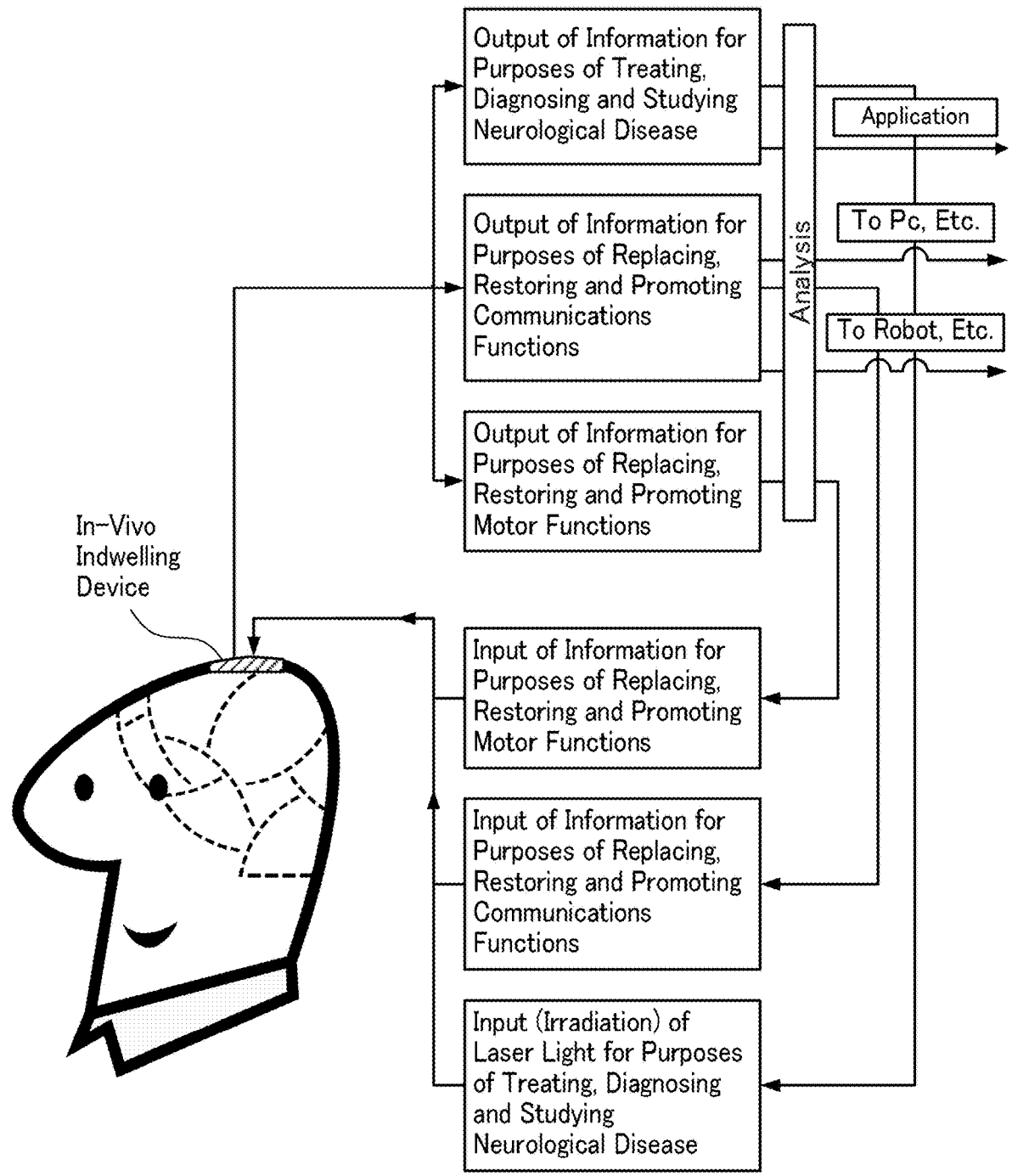

Consequently, as shown in FIG. 7, when the device is indwelled in a living body (such as the brain), it can be used to output and input information for purposes of treating, diagnosing and investigating nervous system disorders (for example, such neurological diseases as Alzheimer's, Parkinson's, Creutzfeldt-Jakob's, dementia and epilepsy). It can also be used to output and input information for purposes of replacing, restoring and promoting communication functions. Moreover, it can be used to output and input information for purposes of replacing, restoring and promoting motor functions. Information from the living body is generally analyzed and then used according to the type of information. Information related to communication functions can be input into a PC or the like and used to ascertain a test subject's intentions or the like. Information related to motor functions can be input into a robot or the like and expressed in terms of robot movement. Such input and output of information and replacement of various functions and the like is also the aim of BMI.

Embodiment

In this embodiment, an opening was formed in a mouse skull, a rare earth doped fluorapatite (Yb:s-FAP, $(Yb_{0.05}Sr_{4.95}(PO_4)_3F)$) was applied to the opening, and biocompatibility was confirmed.

A disk-shaped sintered body 4 mm in diameter and 0.4 mm thick was used as the rare earth doped fluorapatite. This sintered body had a porosity of less than 0.2% and a linear transmittance of at least 50%. Also, the c-axis directions of the apatite were oriented in the direction of thickness.

(1) Preparation of Animal

Figure 8:
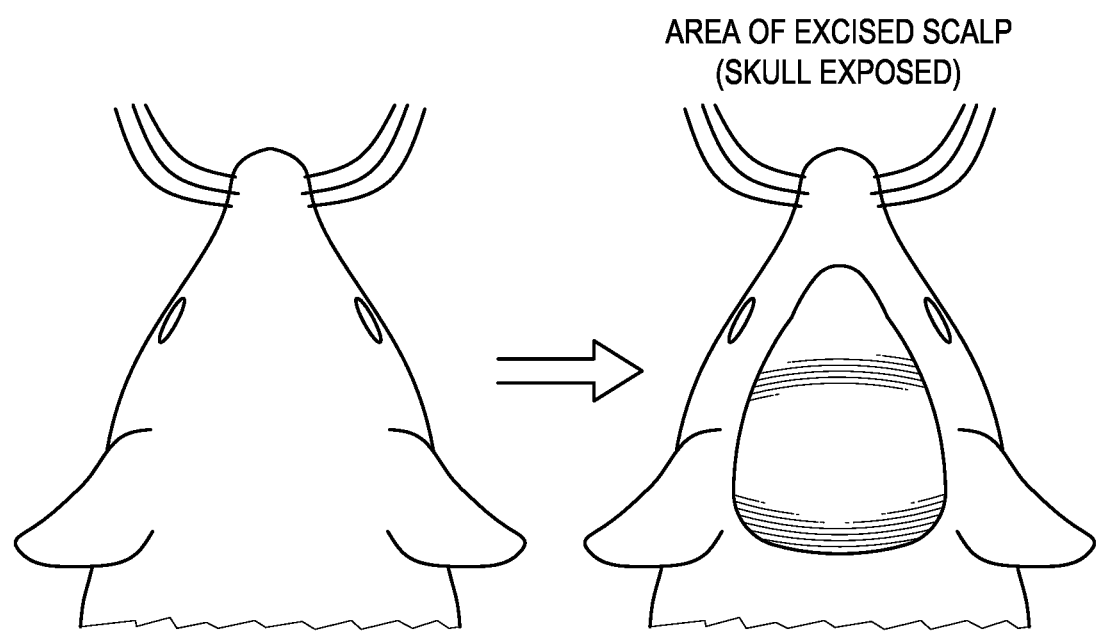
FIG. 8 illustrates a mouse scalp incision of an example.

An 8-week-old male genetically modified mouse (Thy 1-GFP transgenic mouse (M-line)) was subjected to general anesthesia by intraperitoneal administration of ketamine (100 mg/kg) and xylazine (10 mg/kg), the mouse's head was fixed with a stereotaxic instrument (SR-5N, Narishige Co., Ltd.) and ear bars, and the scalp was excised with scissors in the shape shown in FIG. 8 (about 14 mm longitudinally, 10 mm laterally), exposing the skull.

(2) Indwelling of Fluorapatite Disk a) Apatite Placed on Top of Skull

Figure 9:
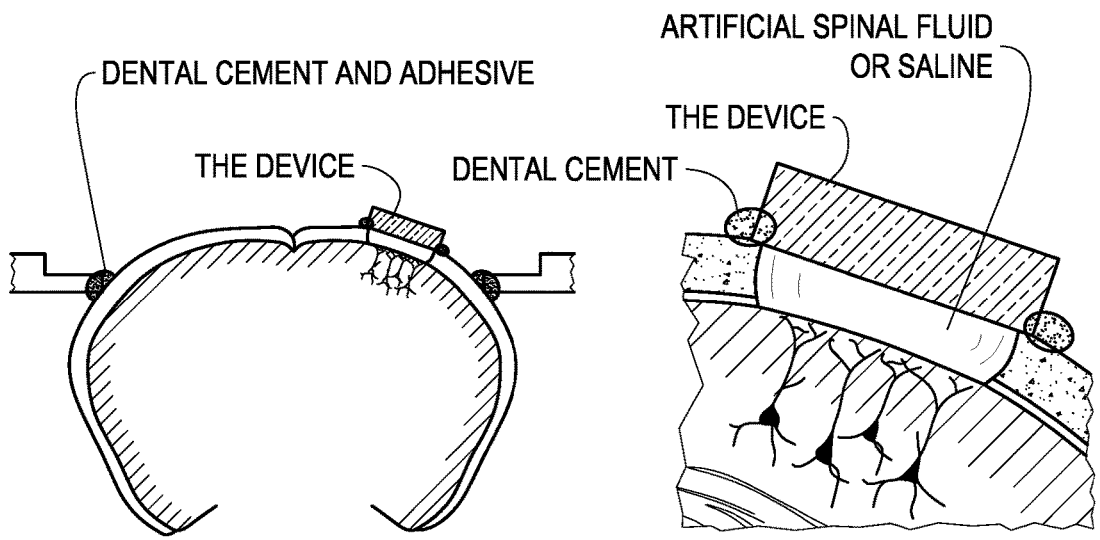
FIG. 9 shows a rare earth doped fluorapatite indwelling in a mouse in an example (placement example)

A dedicated fixing chamber was prepared, and dental cement (Super Bond, Sun Medical Co.) was applied to the fixture and bonded to the skull. Next, the bond was reinforced with an adhesive for living tissue (3M™ Co. Vetbond™). The ear bars were then removed, and the head was fixed by the stereotaxic instrument and fixing chamber. A small drill with a 0.5 mm tip (FST Co, 19007-05 and Narishige Co., Ltd. SD-101) was used to open a hole about 2 to 3 mm in diameter in the skull. Artificial spinal fluid or physiological saline was placed on the brain surface exposed through the opening, and using the disk as a lid, the outer edge of the disk was of to the skull with Super Bond (see FIG. 9). The mouse was returned to its cage without suturing of the scalp.

b) Apatite Inset into Skull

Figure 10:
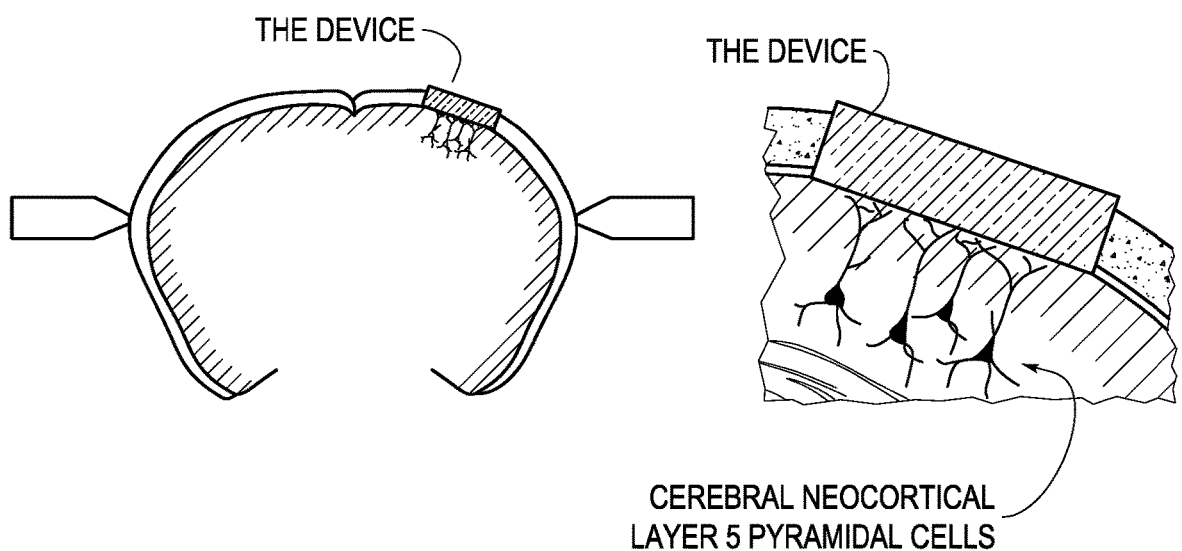
FIG. 10 shows a rare earth doped fluorapatite indwelling in a mouse in an example (inset example example)

With the skull fixed with a stereotaxic instrument and ear bars, a hole 4 mm in diameter was opened in the skull with a small drill, the disk was placed directly on the exposed brain surface, after which the same operations were followed as in a) except that the scalp was sutured, and the mouse was returned to its cage (see FIG. 10). In this case, an opening was formed that was larger than the disk.

Figure 11:
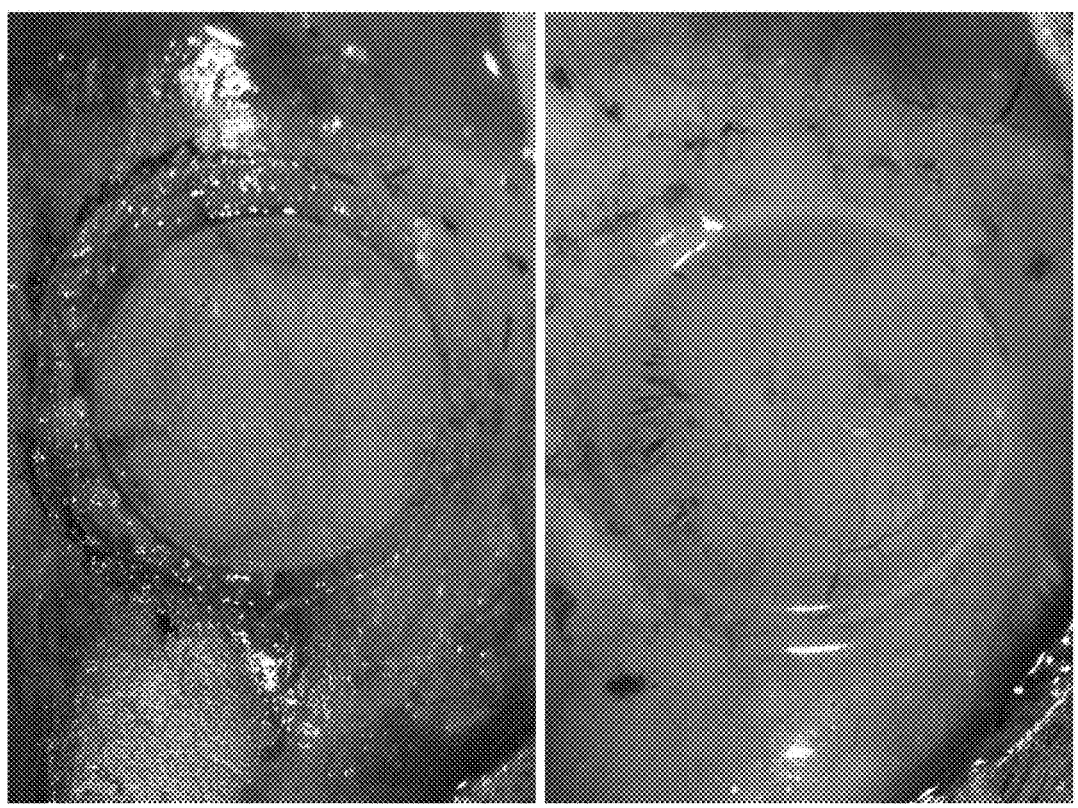
FIG. 11 shows mice 0 and 28 days after indwelling (placement example) and 0 and 21 days after indwelling (inset example).
Figure 11:
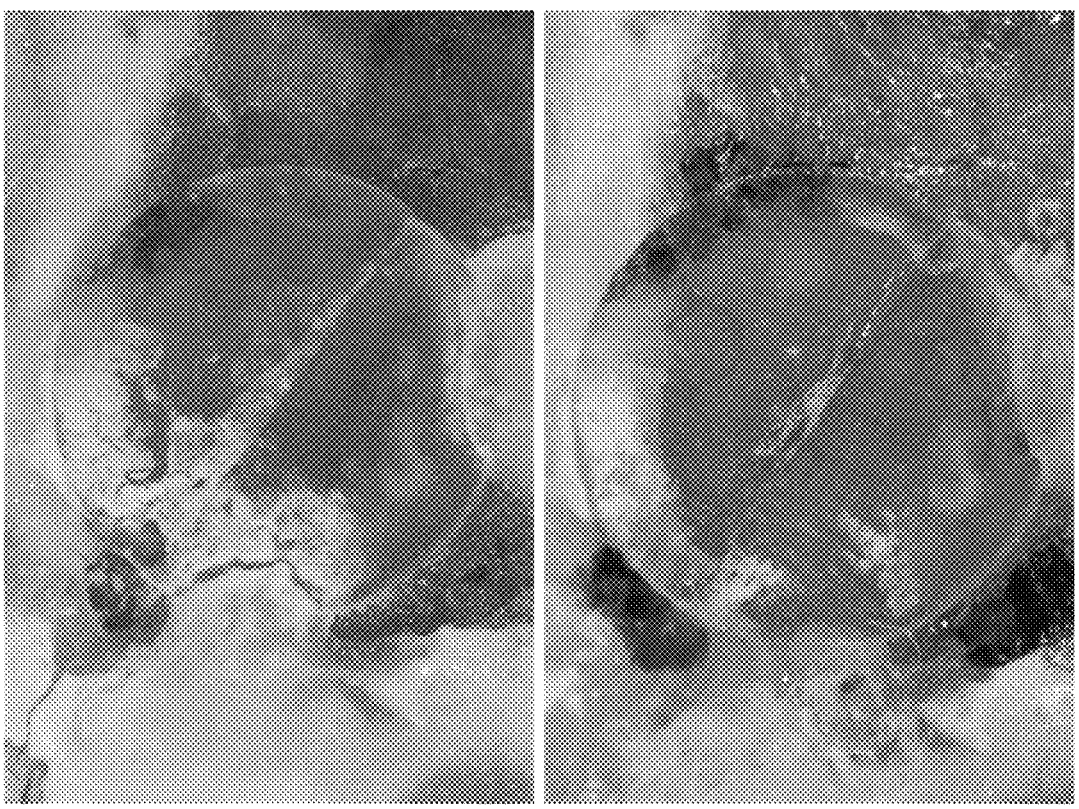

The bone junctions of the fluorapatite disks indwelled in the living mice are shown in FIG. 11. The placement example is shown on the left of FIG. 11, and the inset example on the right. As shown on the left of FIG. 11, in the disk placement example the disk and skull were thoroughly fixed even on day 0 of indwelling. Even after the dental cement was removed after 28 days, the two adhered together well, indicating that the fluorapatite was adhering directly to the skull. The disk did not induce any immune reaction, and the brain surface remained stable. Moreover, the disk maintained good translucency despite exposure to the outside.

Moreover, as shown on the right of FIG. 11, although the disk was not entirely fixed on day 0 of indwelling, by day 21 the membrane tissue had infiltrated between the inner edge of the bone and the outer edge of the disk, and the disk had become fixed inside the opening to a certain degree. In other words, this shows that bone tissue regeneration and bonding had progressed. The disk translucency remained good.

These results show that a rare earth doped fluorapatite has good biocompatibility in vertebrates, and that induction of immune response is suppressed or avoided. Good bone bonding was also observed. Moreover, the translucency of the fluorapatite was stably maintained.

The invention claimed is:

1. A system for inputting or outputting information to and from a brain, the system comprising:
   an optical device configured to replace a part of a skull covering the brain so as to allow the brain to be viewed, the optical device comprising:
      a base material: (i) having a translucent region which is a laser medium and contains a rare-earth doped fluorapatite, and (ii) configured to function as a laser oscillation device;
      an incident mirror disposed on a body surface side of the translucent region opposite to the brain; and
      an exit mirror or a Fresnel reflection disposed: (i) in opposition to the incident mirror, and (ii) on an internal surface side of the translucent region adjacent to the brain, and
      a device configured to: (i) output information via laser light from inside the brain through the translucent region, or (ii) input information via laser light from outside the brain through the translucent region,
   wherein:
      the rare-earth doped fluorapatite contains at least one of Nd and Yb in a single crystal particle of a single crystal fluorapatite or crystal particles of polycrystalline fluorapatite, and
      the rare-earth doped fluorapatite has a porosity of less than 0.2%.

2. The system according to claim 1, wherein the rare earth doped fluorapatite has a linear transmittance of at least 50%.

3. The system according to claim 1, wherein the rare earth doped fluorapatite undergoes laser oscillation upon exposure to a laser.

4. The system according to claim 1, wherein the optical device is a bone replacement device.

5. The system according to claim 1, wherein the optical device is an optical window.

6. The system according to claim 1, wherein:
the translucent region is configured to be placed at a deficient part of a skull that is cut or damaged so as to supplement the deficient part.

7. The system according to claim 1, wherein the rare-earth doped fluorapatite has a porosity of 0.05% or less.

8. The system according to claim 1, wherein the exit mirror is disposed on the internal surface side of the translucent region.

9. The system according to claim 8, wherein the optical device further comprises:
an optical switch disposed on a body surface side of the exit mirror.

10. The system according to claim 9, wherein the exit mirror and the optical switch are disposed: (i) adjacent to each other, and (ii) on the internal surface side of the translucent region.

11. The system according to claim 9, wherein the exit mirror and the optical switch are disposed within a ceramic matrix of the translucent region.

12. The system according to claim 9, wherein the incident mirror, the exit mirror, and the optical switch are disposed within a ceramic matrix of the translucent region.

13. A method for operating the system according to claim 1, the method comprising outputting information from inside the brain via laser light through the translucent region; or inputting information via laser light from outside the brain through the translucent region.

14. A method for inputting and outputting information to and from a brain, the method comprising
replacing a part of a skull covering the brain with an optical device to view the brain, the optical device comprising:
a base material: (i) having a translucent region which is a laser medium and contains a rare-earth doped fluorapatite, and (ii) configured to function as a laser oscillation device;
an incident mirror disposed on a body surface side of the translucent region opposite to the brain; and
an exit mirror or a Fresnel reflection disposed: (i) in opposition to the incident mirror, and (ii) on an internal surface side of the translucent region adjacent to the brain, and
outputting information via laser light from inside the brain through the translucent region; or
inputting information via laser light from outside the brain through the translucent region,
wherein:
the rare-earth doped fluorapatite contains at least one of Nd and Yb in a single crystal particle of a single crystal fluorapatite or crystal particles of polycrystalline fluorapatite, and
the rare-earth doped fluorapatite has a porosity of less than 0.2%.

* * * * *